(12) United States Patent
Stucker

(10) Patent No.: US 9,121,800 B2
(45) Date of Patent: Sep. 1, 2015

(54) INTERNALLY REFLECTIVE CHAMBER FOR FLUORESCENT RADIATION COLLECTION AND CONCENTRATION, AND METHOD FOR USING THE SAME

(71) Applicant: David Stucker, Plainfield, IN (US)

(72) Inventor: David Stucker, Plainfield, IN (US)

( * ) Notice: Subject to any disclaimer, the term of this patent is extended or adjusted under 35 U.S.C. 154(b) by 0 days.

(21) Appl. No.: 14/106,068

(22) Filed: Dec. 13, 2013

(65) Prior Publication Data

US 2014/0217308 A1   Aug. 7, 2014

Related U.S. Application Data

(60) Provisional application No. 61/755,165, filed on Jan. 22, 2013, provisional application No. 61/736,749, filed on Dec. 13, 2012.

(51) Int. Cl.
*G01N 15/14* (2006.01)
*G01N 21/64* (2006.01)
*G01N 15/10* (2006.01)

(52) U.S. Cl.
CPC ........ *G01N 15/1434* (2013.01); *G01N 15/1459* (2013.01); *G01N 2015/1006* (2013.01); *G01N 2021/6421* (2013.01)

(58) Field of Classification Search
CPC .......... G01N 15/1459; G01N 15/1434; G01N 21/645; G01N 2021/6421; G01N 2015/10061
See application file for complete search history.

(56) References Cited

U.S. PATENT DOCUMENTS

| | | | |
|---|---|---|---|
| 5,999,250 A * | 12/1999 | Hairston et al. | 356/73 |
| 2003/0054558 A1* | 3/2003 | Kurabayashi et al. | 436/63 |
| 2006/0192940 A1* | 8/2006 | Phi-Wilson | 356/73 |
| 2007/0229825 A1* | 10/2007 | Bates | 356/339 |
| 2009/0158823 A1* | 6/2009 | Kaduchak et al. | 73/61.75 |
| 2009/0325192 A1* | 12/2009 | Kirakossian et al. | 435/7.2 |

* cited by examiner

*Primary Examiner* — Yara B Green
(74) *Attorney, Agent, or Firm* — C. John Brannon; Brannon Sowers and Cracraft PC

(57) ABSTRACT

A system for collecting and analyzing maximized amounts of fluorescent radiation using frequency scattering ports or waveguides that absorb a desired size of wavelengths.

11 Claims, 5 Drawing Sheets

INTERNALLY REFLECTIVE CHAMBER FOR FLUORESCENT RADIATION COLLECTION AND CONCENTRATION, AND METHOD FOR USING THE SAME

CROSS-REFERENCE TO RELATED APPLICATIONS

This application claims priority to U.S. provisional patent application Ser. No. 61/736,749, filed Dec. 13, 2012; and U.S. provisional patent application Ser. No. 61/755,165, filed Jan. 22, 2013, each of which are incorporated herein in their entirety by reference.

TECHNICAL FIELD

The present novel technology relates to the field of laser physics, and, more particularly, to a laser-based cytometer flow measurement system.

BACKGROUND

In the field of cytometry, collection and analysis of fluorescent radiation is important. Cells or particles of interest are bound with various fluorescent tags and generally sent via fluidic transport through an interrogation point, where the particles are then illuminated such as by a laser or other light source. Given an appropriate tag that will interact with the incident wavelength of light, the particles will then radiate a fluorescent signal that indicates a particular trait held by the particles in interest. This signal is then processed through an optical train, typically consisting of a combination of lenses, fibers and/or dichroic mirrors to relay the fluorescent signal to a final detector to be captured. Overall, flow cytometers collect a relatively small amount of the omitted fluorescent signal. This weak signal necessitates the use of photomultiplier tubes (PMTs) for the direct measurement of the fluorescent signal, necessitating yet further amplification of the PMT's output for subsequent sample characterization. The desire to increase the amount of fluorescent radiation collected is very great, and has generated considerable work and various approaches to reaching this elusive goal. Simply stated, increasing the amount of fluorescent radiation collected for analysis will allow lower threshold levels of radiation to be measured, thereby boosting the number of particles in interest observed and increasing the probability of detecting sporadic or rare events held within the sample set. Conventional commercial flow cytometers typically utilize high numerical aperture optics to collect the fluorescent radiation for analysis. This technique limits the amount of radiation that can be collected by constraining the volume of the fluorescence emitted for observation to that of the numerical aperture optics used. If there was a way to collect and analyze a greater amount of the fluorescent radiation signal, it would be possible to better track the presence of certain cells in health or cancer research, or increase accuracy when conducting research into biomarkers, and gain better feedback for protein engineering, and the like. Thus, a need persists for a more effective technique for capturing and utilizing a greater portion of the generated fluorescent signal during cytometric analysis. The present novel technology addresses this need.

DESCRIPTION OF THE PREFERRED EMBODIMENTS

Figure 2:
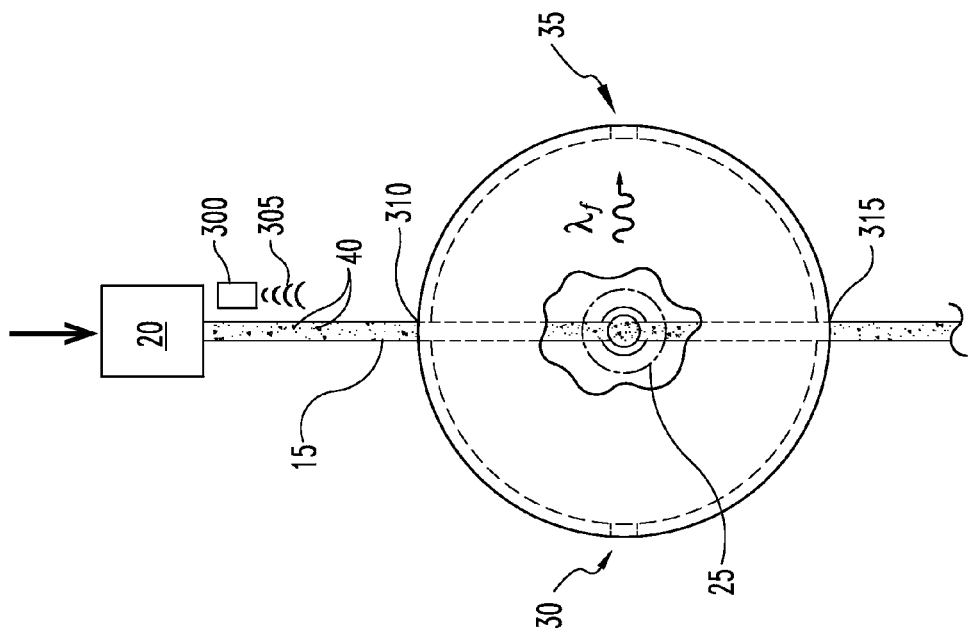
FIG. 2 is a schematic front sectional view of the internally reflective chamber for fluorescent radiation collection and concentration, of FIG. 1.

For the purposes of promoting an understanding of the principles of the novel technology and presenting its currently understood best mode of operation, reference will now be made to the embodiments illustrated in the drawings and specific language will be used to describe the same. It will nevertheless be understood that no limitation of the scope of the novel technology is thereby intended, with such alterations and further modifications in the illustrated device and such further applications of the principles of the novel technology as illustrated therein being contemplated as would normally occur to one skilled in the art to which the novel technology relates.

In traditional cytometer flow cell architecture, a very small percentage of the fluorescent radiation generated by the sample being investigated is collected usefully. The novel technology presented herein relates to a method and apparatus for the collection of most or virtually the entire radiation signal generated by fluorescing a sample material and/or maximizes the collected signal to increase detection capabilities. The novel technology operates to encase the point of fluorescence in a hollow reflective chamber wherein the emitted radiation is redirected and/or concentrated for measurement and analysis. The basic configuration from an optical component manufacturing or light manipulation standpoint is typically spherically based, more typically an integration sphere or partial sphere to encase the point of fluorescence. To concentrate and direct the fluorescent radiation emitted during cytometry, the integration sphere is typically truncated to become a highly reflective hemisphere and then conjoined with a high collection, non-imaging reflective optical component with a singular circular output. To increase collection and light concentration efficiency, the profile of this non-imaging reflective component is typically determined to be a hyperboloid of revolution, as this shape lends itself to useful radiation concentration. As an added benefit, the light emitted from the hyperboloid of revolution is very well-behaved and lends itself nicely to manipulation and transmission. This design and functionality applies to either the hollow core or optically transparent solid core versions of the flow cell chamber.

While fluorescence measurement is one useful aspect of flow cytometry analysis, forward scatter (FS) and side scatter (SS) measurements may be equally useful. The design disclosed herein also addresses these measurements as well. Dependent upon the particular version of the chamber selected, ports may be either machined directly into the chamber (hollow core) or machined into the lower index coating material (solid core) such that the traditional methods of FS and SS measurements still apply.

Figure 1:
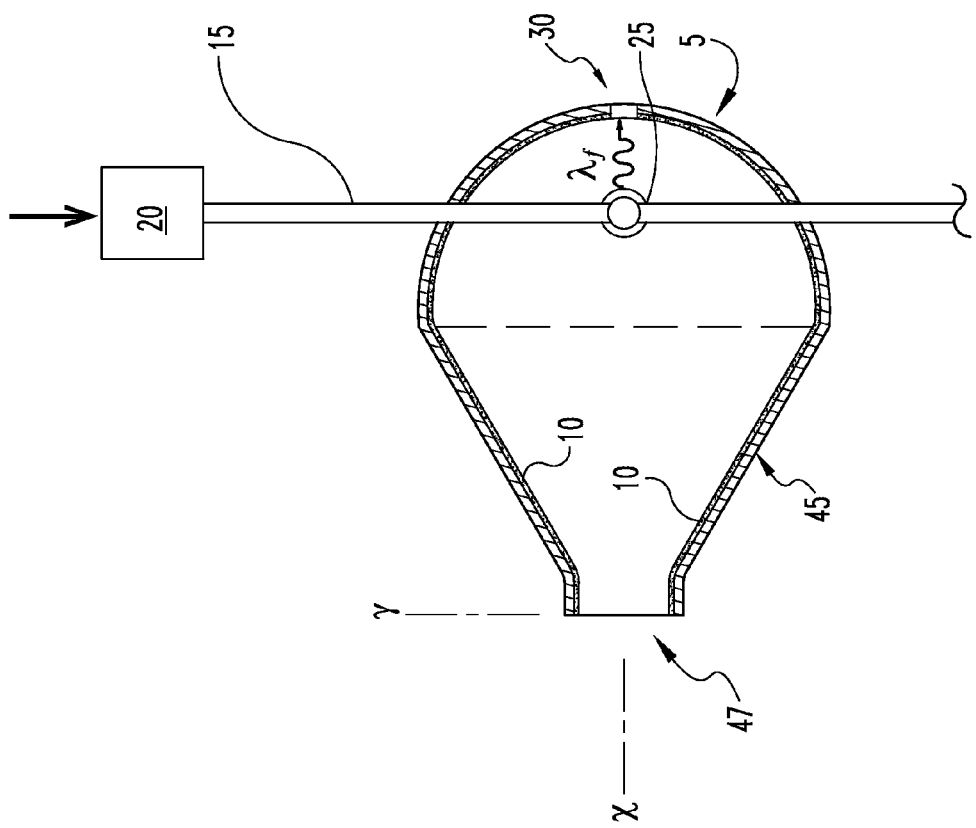
FIG. 1 is a schematic side sectional view of the internally reflective chamber for fluorescent radiation collection and concentration, according to the first embodiment of the present novel technology.

One embodiment of the novel technology as illustrated in FIG. 1 and FIG. 2 is a flow cytometer 1 having an internally reflective, generally hollow chamber 5 in which a sample may be laser fluoresced with the fluorescent radiation collected and concentrated. The chamber 5 typically either inherently reflective or has the shape of a hemisphere and functions as a high collection, non-imaging reflector. The chamber 5 is typically internally coated 10 with broadband reflective material, the selection of which is typically substrate dependent and of a lower index material. A capillary transport 15 is positioned at one or more predetermined locations within the chamber 5 to supply particles 40 from a flow cell 20, which is typically positioned outside the chamber 5, through a focus position 25 of an operationally connected integration laser 30, likewise typically positioned outside the cell. The focus potion 25 is typically centrally positioned inside the chamber 5. Frequency scattering ports 35 are typically positioned around the chamber 5 to facilitate laser focus as well as forward and side scatter detection. The ports 35 for laser 30 introduction and the forward scatter measurement typically lie in a line that intersects the focus position 25 of the hemisphere. The side scatter port 35 and focal position 25 of the hemisphere 5 typically lie in a line orthogonal to the line formed by the laser(s) (or light) port, focal point of the hemisphere 5, and the forward scatter port. Particles emitted from the particle interrogation position 25 are collected by reflection and emitted out of the non-imaging reflector output portion 45. The new imaging reflector output portion 45 is operationally connected in photonic communication with the hemisphere chamber 5 to guide and concentrate fluoresced signals from the particles to an output port 47. The output portion 45 typically has the shape of a hyperboloid of revolution, although it may have any convenient shape. The collected particles 40 is then evaluated according to methods commonly used in the art, such as spectrometry or other like means of evaluation or measurement. Fiber optic conduits (not shown) may also be used to transport the input or output of particles 40 of the chamber 5. Additional observation ports 35 may be added to the chamber 5 to allow further imaging of the interrogation point 25.

Figure 4:
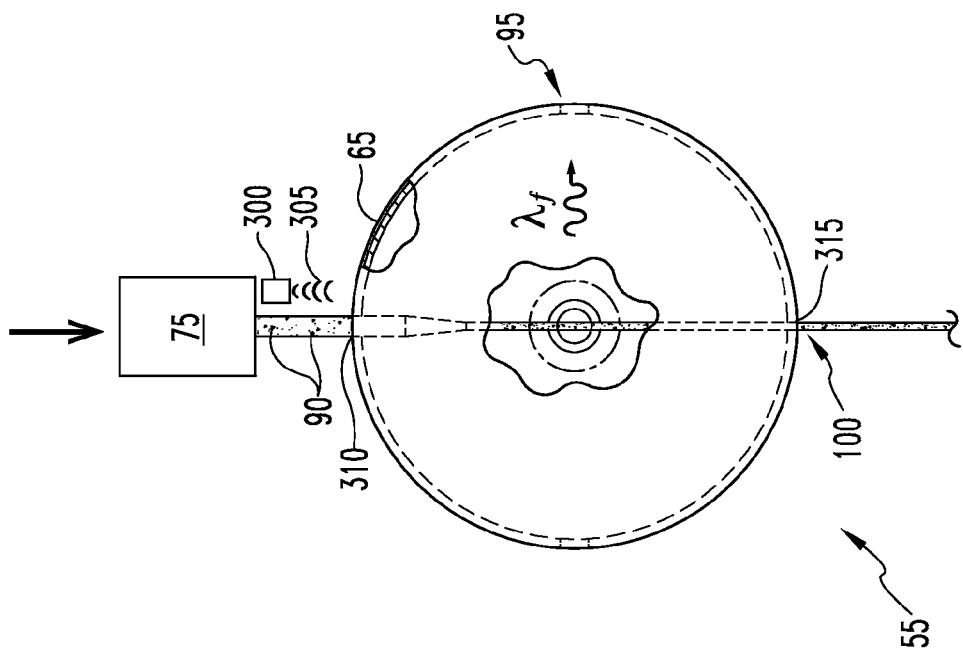
FIG. 4 is a diagram of the solid externally reflective flow cell for the collection and concentration of fluorescent radiation.
Figure 3:
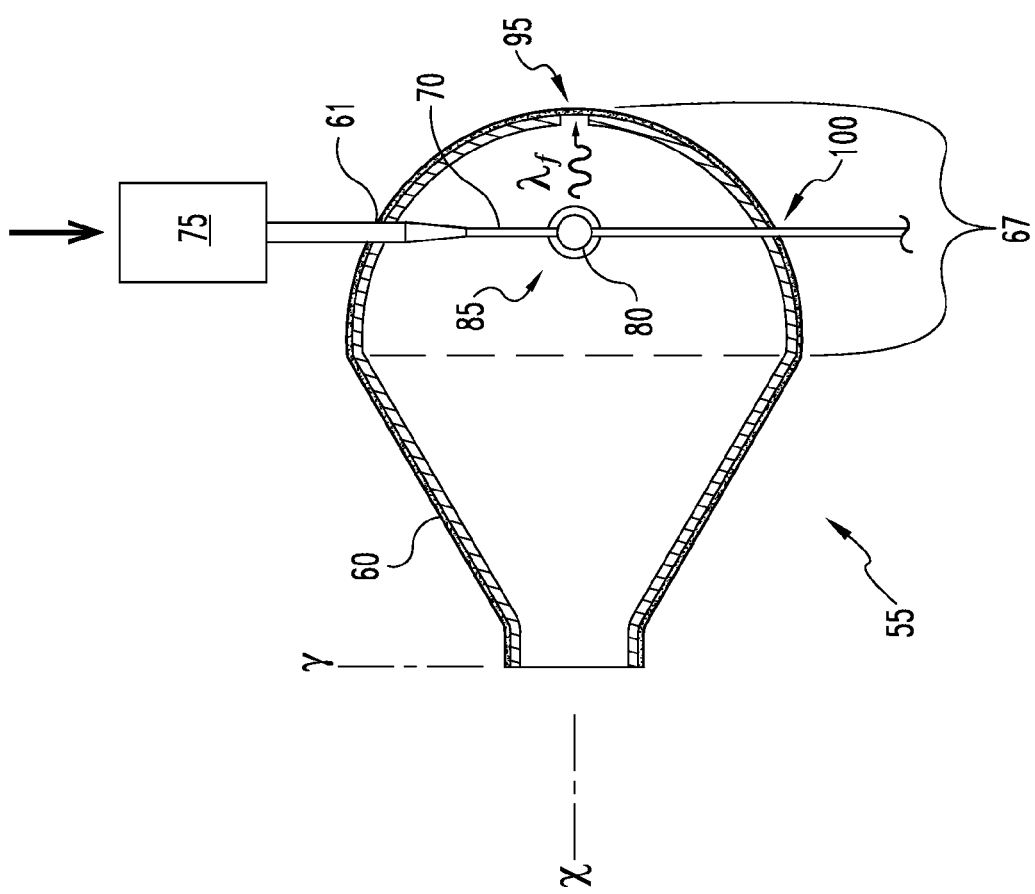
FIG. 3 is a schematic side sectional view of a solid externally reflective flow cell for the collection and concentration of fluorescent radiation, according to the second embodiment of the present novel technology.

A second embodiment of the instant novel technology, as illustrated in FIG. 3 and FIG. 4, is a flow cytometry system 55 having an externally reflective chamber 60. The solid, optically transparent externally reflective chamber 60 is typically a unitary combination of an integration hemisphere 67 cojoined with a high collection, non-imaging hyperboloid of revolution reflector with material selected for broad wavelength transmission. The chamber 60 is typically externally coated 65 for broadband internal reflection. The chamber 60 includes a generally cylindrical elongated conduit 61 formed there through. A capillary transport 70 extends through the conduit 61 within the chamber 60 to supply particles 90 from a flow cell 75, which is positioned outside the chamber 60 and in fluidic communication with the capillary transport system 70, through a focus position 80 of an operationally connected interrogation laser 85, likewise typically positioned outside the cell. The focus position 80 is typically strategically positioned inside the conduit 61. Frequency scattering ports 95 through the coating 65 are located at the preselected positions on the hemisphere 67 to allow laser 85 focus as well as forward and side scatter detection. The ports 95 for laser 85 introduction and the forward scatter measurement lie in a line that contains the focal point 80 of the hemisphere 87. The side scatter port and focal point 80 of the hemisphere 87 typically lie in a line orthogonal to the line intersecting the laser 85 port, focal point 80 of the hemisphere 87, and the forward scatter port 95. Photons 90 emitted from the particle interrogation position 80 are collected by reflection and emitted out of the non-imaging reflector output positions 100. The collected photons 90 may then be evaluated though methods commonly used in the art such as a spectrometer or other means of evaluation or measurement. As with the previous embodiment, fiber optic conduits 50 may also be used to transport the photon 90 input or output of the chamber 60. An example of a possible coating 10,65 material for the first and second embodiment would be aluminum, which may increase reflectivity to at least 60% more typically at least 70%, still more typically at least 80%, and even up to at least 90%, allowing close to the theoretical maximum amount of fluorescent energy to be collected for analysis.

Figure 5:
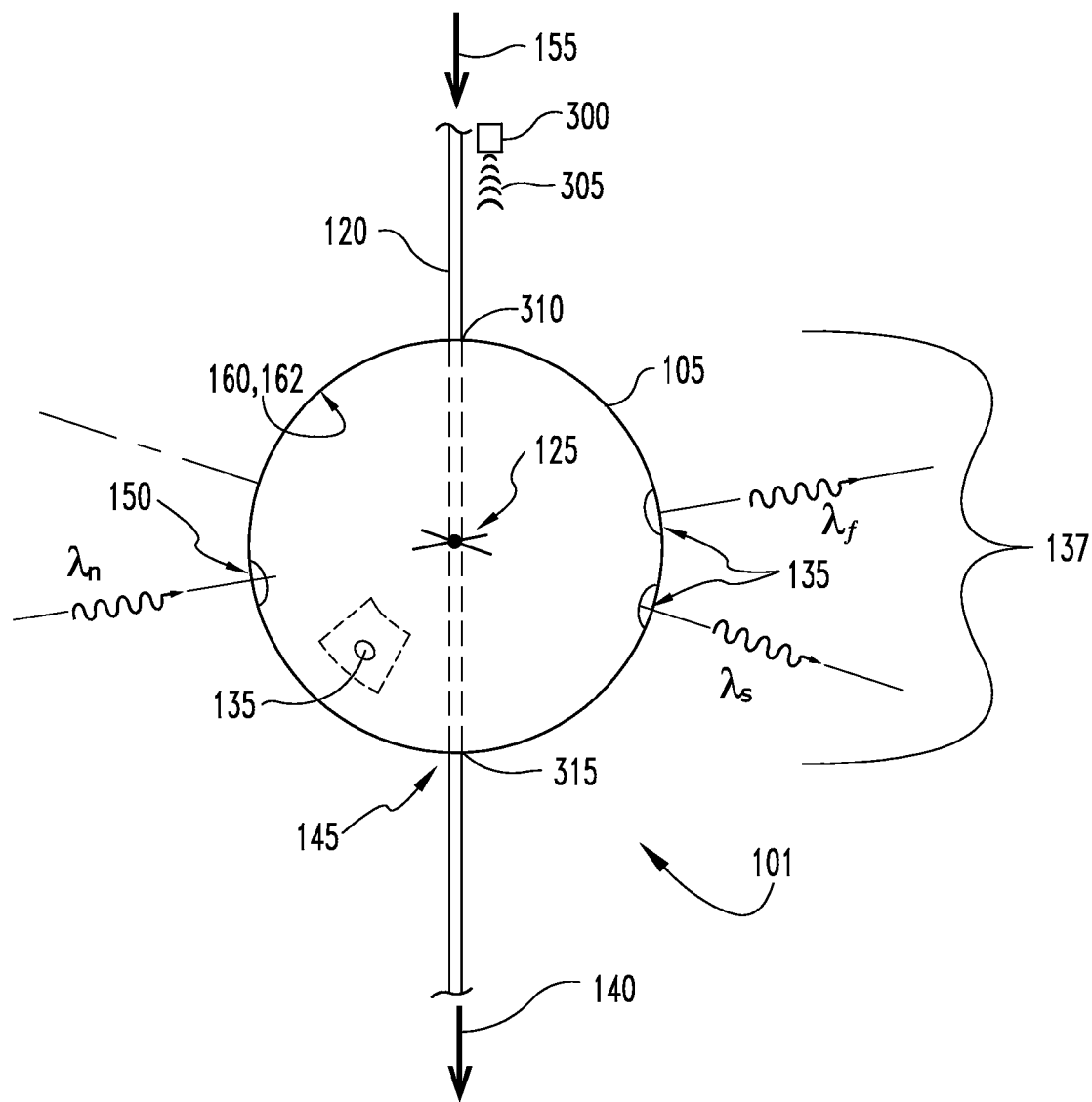
FIG. 5 is a schematic view of a spherical florescent radiation detector cell, of the present novel technology.

A third embodiment, illustrated in FIG. 5, is a flow cytometry system 101 having a generally spherical reflective chamber 105. The spherical reflective chamber 105 operates much like the above described first and second embodiments, but the spherical shape allows for possible alternative observation strategies for collection of the forward and side scatter of particles 140 through the input and output ports. Similar to the first and second embodiments, capillary tubing 120 provides the input and output of the flow cell 155 via a capillary 120 channel through the center of the cell. The capillary transport is positioned in the center of the spherical chamber 105, to supply particles 140 from a flow cell 155, which is positioned outside the chamber 105, through a focus position 125 of the integration laser 130. Frequency scattering ports 135 are typically located at the appropriate positions on the sphere to allow laser 130 focus as well as forward and side scatter detection ports 135. The ports 150 for light beam introduction and the forward scatter measurement typically lie in a line that contains the focal point 125 of the sphere 137. The side scatter port 135 and focal position 125 of the hemisphere lie in a line intersecting the laser port 150, focal point of the hemisphere 125, and the forward scatter port 135. Optional ports can be added for direct imaging of the interrogated particles 140. Particles 140 emitted from the particle interrogation position 125 are collected by reflection and emitted out of the non-imaging reflector output positions 145. The collected particles 140 can then be evaluated though methods commonly used in the art such as a spectrometer or other means of evaluation or measurement. The surface of the sphere is typically covered with a pixelated multispectral wavelength detector 160 to capture the particles released from the chamber 105. The pixelated multispectral wavelength detector 160 typically encapsulates the entire spherical chamber 105 in its entirety, but for the side and forward scattering observation ports 135 left clear for observation analysis. Alternatively, the chamber 105 may be coated with a broadband anti-reflective coating 162, to restrain the radiation 140 in the chamber 105, if no measuring device is encapsulating the chamber 105 for particle 140 analysis. Fiber optics 50 may also be used to transport the input or output of the chamber 105. Additional observation ports 135 may be added to the chamber 105 to allow imaging of the interrogation point 125.

In any of the above embodiments, an ultrasonic transducer 300 can be used to generate ultrasonic waves 305 to guide particle 40, 90, 140 flow such that corresponding ultrasonic wave pressure acts as a gate allowing particles to pass through the focal point 25, 80, 125 individually. The particles 40, 90, 140 may be injected into the embodiment 1, 55, 101 at an input point 310 between the ultrasonic transducer 300 and the focal point 25, 80, 125. Once the particles 40, 90, 140 are aligned past the focal point 25, 80, 125, the separated particles 40, 90, 140 and may be evaluated from the output ports 315 though methods commonly used in the art such as a spectrometer or other means of evaluation or measurement.

Figure 6:
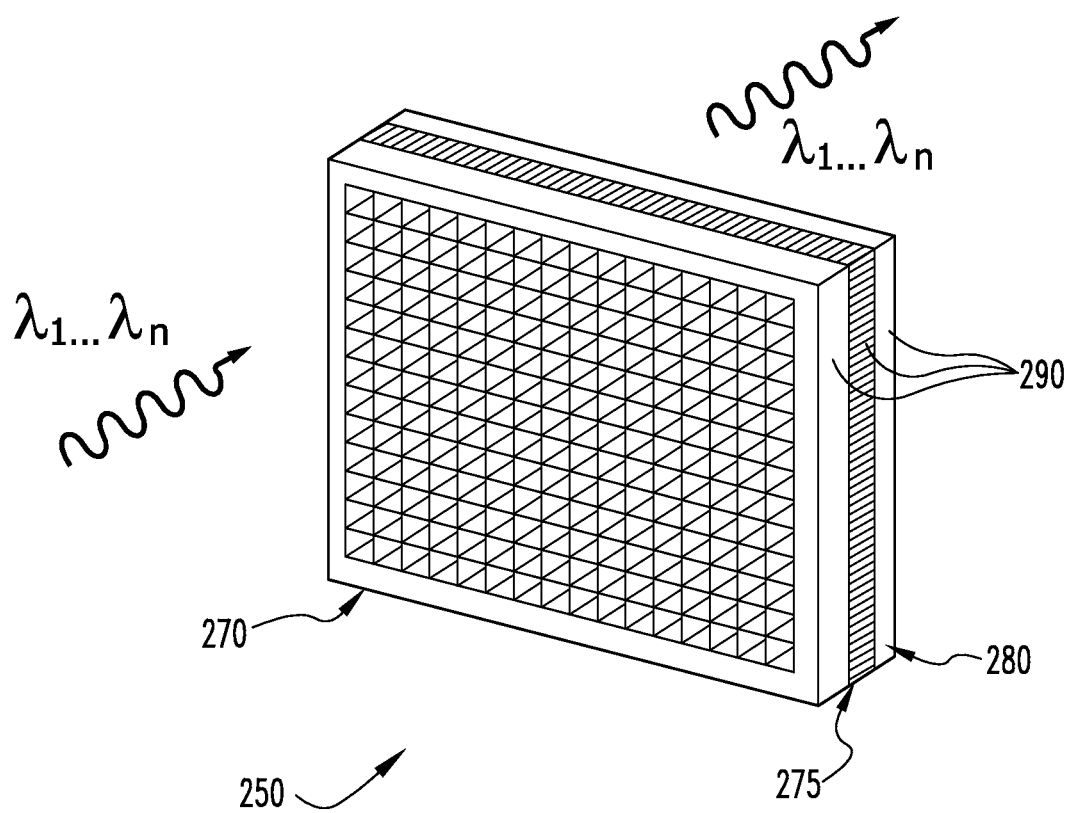
FIG. 6 is a schematic diagram of a multispectral wavelength selective detector, for use with the present novel technology.
Figure 7:
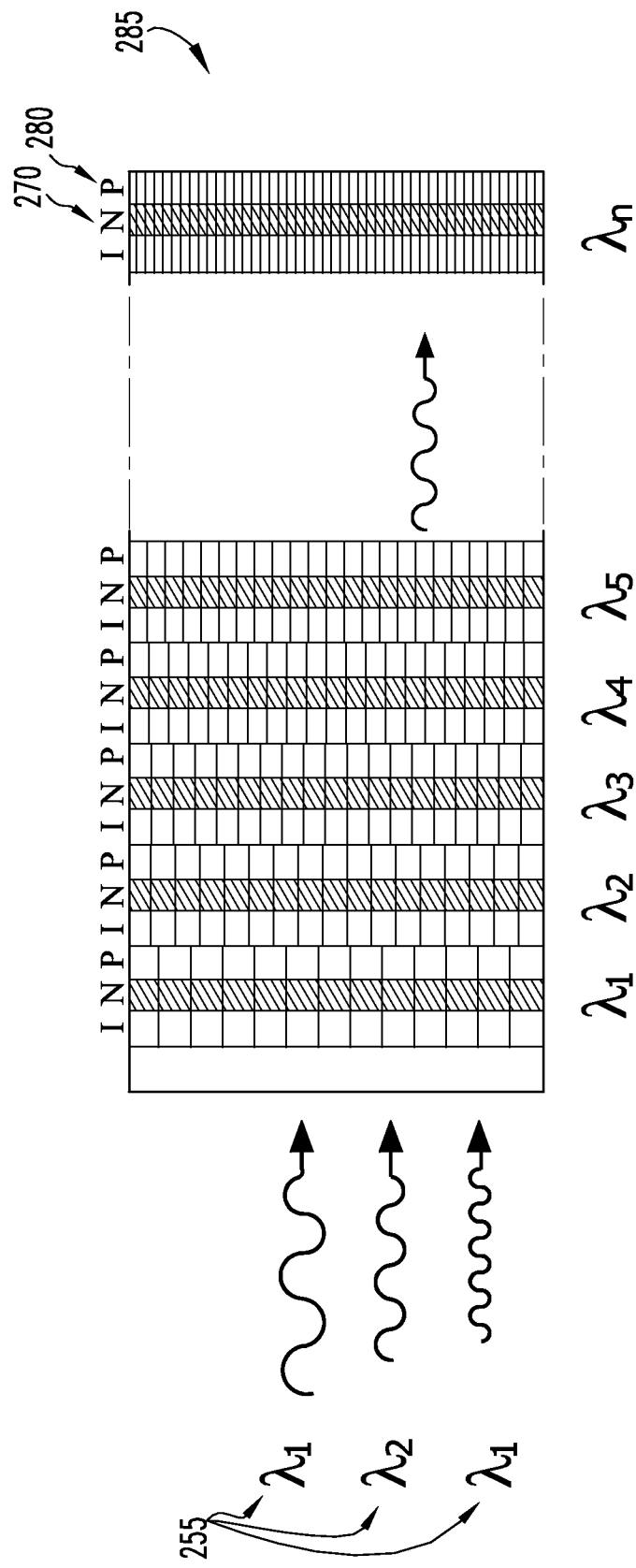
FIG. 7 is a schematic diagram of the pixelated architecture of the multispectral wavelength selective detector of FIG. 6.

A fourth embodiment useful for assisting in spectral analysis of fluorescent radiation as generated and connected in the above cytometry systems 1, 55, 101, illustrated in FIG. 6 and FIG. 7, is a multispectral wavelength selective detector 250 made of multiple layers of waveguides 290. The layers of waveguides 290 are dimensionally sized to either allow the transmission of incident wavelengths 255, to be collected for analysis later, or absorption of a selected wavelength 255 for measurement. Longer wavelengths 255 are measured toward the input 265 of the detector, with shorter wavelengths measured by layers father into the lights path's penetration into the detector 250. The layers 290 are composed of alternating insulator 270 layer, N layer 275 then P layer 280 repeatedly stacked in consecutive order. Coatings may be applied to the waveguide 290 layers to increase light transmission into the detector 250. Overall waveguide 290/detector 250 construction is of a pixelated architecture 285. The detector 250 can be used to encapsulate reflective chambers, such as those described by the third embodiment, to analyze the particles released from the chamber. This detector 250 architecture may be applied to other measurement or observation methods for wavelength 225 analyses.

It will be appreciated that several of the above-disclosed and other features and functions, or alternatives thereof, may be desirably combined into many other different systems or applications. Also, that various presently unforeseen or unanticipated alternatives, modifications, variations or improvements therein may be subsequently made by those skilled in the art which are also intended to be encompassed by the following claims.

While the claimed technology has been illustrated and described in detail in the drawings and foregoing description, the same is to be considered as illustrative and not restrictive in character. It is understood that the embodiments have been shown and described in the foregoing specification in satisfaction of the best mode and enablement requirements. It is understood that one of ordinary skill in the art could readily make a nigh-infinite number of insubstantial changes and modifications to the above-described embodiments and that it would be impractical to attempt to describe all such embodiment variations in the present specification. Accordingly, it is understood that all changes and modifications that come within the spirit of the claimed technology are desired to be protected.

What is claimed is:

1. A cytometric system for fluorescent radiation concentration and collection, comprising:
    a generally hemispheric internally reflective chamber;
    a capillary transport system intersecting the internally reflective chamber;
    a flow cell positioned in fluidic communication with the capillary transport system for storing and releasing a plurality particles through the capillary transport system;
    a particle interrogation position located in the chamber;
    an interrogation laser positioned to shine on the particle interrogation position;
    at least one input port formed in the internally reflective chamber;
    a non-imaging reflector output portion formed operationally connected to the generally hemispheric internally reflective chamber; and
    an output port formed in the non-imaging reflector output portion;
    wherein the non-imaging reflector output portion is hyperbolic in shape;
    wherein the flow cell may be actuated to supply a stream of particles to the particle interrogation position; and
    wherein each respective particle occupying the particle interrogation position is fluoresced by the laser to emit a fluorescent signal to the non-imaging reflector output port.

2. The system of claim 1 wherein the surface of the reflective chamber is coated with broadband reflective material.

3. The system of claim 1 and further comprising at least one frequency scattering port formed in the internally reflective chamber for laser focus, forward scatter detection, and/or side scatter detection.

4. The system of claim 1 and further comprising a particle transport aid operationally connected to the capillary transport system, wherein the capillary transport aid is selected from the group including fiber optics, ultrasonic generators, and combinations of thereof.

5. The system of claim 1 and further comprising additional observation ports for imagining of the interrogation position.

6. A cytometric system for fluorescent radiation concentration and collection, comprising:
    a generally solid, optically transparent, at least partially spherical externally reflective chamber;
    a capillary transport system intersecting the externally reflective chamber;
    a flow cell positioned in fluidic communication with the capillary transport system for storing and releasing a plurality particles through the capillary transport system;
    a particle interrogation position defined positioned in the chamber;
    an interrogation laser positioned to shine on the particle interrogation position;
    at least one input port formed in the chamber;
    a non-imaging reflector output portion formed operationally connected to the chamber; and
    an output port formed in the non-imaging reflector output portion;
    wherein the flow cell may be actuated to supply a stream of particles to the particle interrogation position;
    wherein the output portion is hyperbolic in shape; and
    wherein each respective particle occupying the particle interrogation position is fluoresced by the laser to emit a fluorescent signal to the non-imaging reflector output port.

7. The system of claim 6 wherein the surface of the reflective chamber is coated with broadband anti-reflective material.

8. The system of claim 7 and further comprising at least one frequency scattering port formed through the broadband anti-reflective material for laser focus, forward scatter detection, and/or side scatter detection.

9. The system of claim 6 and further comprising a particle transport aid operationally connected to the capillary transport system, wherein the capillary transport aid is selected from the group including fiber optics, ultrasonic generators, and combinations of thereof.

10. The system of claim 6 and further comprising additional observation ports operationally connected to the chamber for imagining of the interrogation position.

11. The system of claim 6 wherein chamber is spherical in shape.

* * * * *